US012447283B2

(12) United States Patent
Hellström et al.

(10) Patent No.: US 12,447,283 B2
(45) Date of Patent: Oct. 21, 2025

(54) NEEDLE SHIELDING DEVICE

(71) Applicant: Vigmed AB, Helsingborg (SE)

(72) Inventors: Maria Cecilia Therese Hellström, Lomma (SE); Ulf Magnus Handberg, Upplands Väsby (SE); Johan Fredrik Thörne, Helsingborg (SE)

(73) Assignee: Vigmed AB (SE)

( * ) Notice: Subject to any disclaimer, the term of this patent is extended or adjusted under 35 U.S.C. 154(b) by 629 days.

(21) Appl. No.: 17/910,123

(22) PCT Filed: Mar. 4, 2021

(86) PCT No.: PCT/SE2021/050193

§ 371 (c)(1),
(2) Date: Sep. 8, 2022

(87) PCT Pub. No.: WO2021/183024

PCT Pub. Date: Sep. 16, 2021

(65) Prior Publication Data

US 2023/0107871 A1 Apr. 6, 2023

(30) Foreign Application Priority Data

Mar. 10, 2020 (SE) .................................. 2050266-2

(51) Int. Cl.
*A61M 5/32* (2006.01)
*A61M 25/06* (2006.01)

(52) U.S. Cl.
CPC .......... *A61M 5/32* (2013.01); *A61M 25/0606* (2013.01)

(58) Field of Classification Search
CPC ........................... A61M 5/32; A61M 25/0606
See application file for complete search history.

(56) References Cited

U.S. PATENT DOCUMENTS 5,562,631 A * 10/1996 Bogert .............. A61M 25/0631 604/263
5,688,249 A 11/1997 Chang
(Continued)

FOREIGN PATENT DOCUMENTS

CN 105377150 A 3/2016
CN 106730139 A 5/2017
(Continued)

OTHER PUBLICATIONS

Chinese Office Action, CN202180019424.0, dated Jan. 16, 2025 (with machine translation).
(Continued)

*Primary Examiner* — Dung T Ulsh
(74) *Attorney, Agent, or Firm* — Fishman Stewart PLLC

(57) ABSTRACT

The present disclosure discloses a needle shielding device for a catheter instrument extending along a longitudinal axis A, comprising an inner part comprising an inner part track extending along said axis A, a middle part comprising a middle part track extending along the axis A, and an internal middle part engagement, an outer grip part, comprising a needle hub, holding a needle extending along the axis A, and grip part internal engagement. The grip part internal engagement is configured to slidingly engage the middle part track, and the middle part engagement is configured to slidingly engage the inner part track such that the inner part, the middle part and the grip part are telescopingly slidable in relation to one another.

19 Claims, 10 Drawing Sheets

(56) References Cited

U.S. PATENT DOCUMENTS

| | | | | |
|---|---|---|---|---|
| 5,951,523 | A * | 9/1999 | Osterlind .......... | A61M 25/0631 604/198 |
| 6,379,332 | B1 | 4/2002 | Van Landuyt | |
| 2007/0191776 | A1 * | 8/2007 | Bialecki ............ | A61M 25/0631 604/164.08 |
| 2009/0326477 | A1 | 12/2009 | Liversidge | |
| 2011/0288482 | A1 | 11/2011 | Farrell | |
| 2020/0197035 | A1 | 6/2020 | Ravikumar | |

FOREIGN PATENT DOCUMENTS

| | | | |
|---|---|---|---|
| EP | 0374451 | A1 | 6/1990 |
| EP | 0734739 | A2 | 10/1996 |
| EP | 0747087 | A2 | 12/1996 |
| EP | 1352668 | A2 | 10/2003 |
| EP | 1374942 | A1 | 1/2004 |
| EP | 1389991 | A2 | 2/2004 |
| EP | 3260157 | A1 | 12/2017 |
| WO | 02087659 | A2 | 11/2002 |
| WO | 2004045701 | A1 | 6/2004 |

OTHER PUBLICATIONS

International Search Report, PCT/SE2021/050193, dated Mar. 31, 2021.

Chinese Office Action, CN202180019424.0, dated Jan. 12, 2024 (with translation).

* cited by examiner

NEEDLE SHIELDING DEVICE

CROSS-REFERENCE TO RELATED APPLICATIONS

This application is a National Stage Patent Application of International Patent Application No. PCT/SE2021/050193, filed Mar. 4, 2021, which claims the benefit of Swedish Application Serial No. 2050266-2, filed Mar. 10, 2020, the contents of each are incorporated by reference in their entireties.

TECHNICAL FIELD

The present disclosure relates to a needle shielding device. Further, the disclosure relates to a catheter instrument comprising a catheter assembly said needle shielding device.

BACKGROUND

The clinical utilization of a pointed hollow needle mounted inside a flexible catheter tube is well known in the medical art for the introduction of a catheter. In such a medical instrument, the catheter tube is positioned tightly around the needle in such a way as to allow the needle to slide along the length of the catheter tube. Before use, the tip of the needle is protruding slightly through the opening of the catheter tube to allow facile penetration through the skin. Upon puncturing of the skin and introduction of the needle, the distal end of the catheter tube is simultaneously brought into place inside the desired target body cavity of the patient, such as the inside of a blood vessel, for example a vein. The needle has then done its duty in assisting the introduction of the catheter and is withdrawn by being pulled backwards through the catheter. Upon release of the needle, the catheter is set in its intended working mode extending over a lengthier period of time and including, for example, periodical administration or infusion of fluids or medications in liquid form, the collection of blood samples and the like.

An unprotected released needle constitutes, however, a serious health hazard due to the fact that it may be contaminated with e.g. infectious agents originating from the patient's blood or other body fluids, in combination with the needle tip's inherent ability to easily penetrate skin. Hence, the medical personnel who are handling the released needle may acquire the corresponding disease, e.g. HIV or hepatitis, if by accident contacting it with their skin. In order to circumvent or alleviate the health hazards associated with such a released needle amongst other things, there has been much effort devoted to the development of various kinds of needle protectors with a special focus on automatic variants of a type which may be referred to as being "foolproof".

Several solutions for the protection of needle tips are have been presented. For instance, U.S. Pat. No. 6,616,630 B1 discloses a safety IV catheter comprising a resilient spring clip normally positioned in the catheter hub. The needle of the safety IV catheter passes through a hole in the spring clip, which allows axial movement of the needle. When the needle is in the forward position, i.e. when the safety IV catheter is ready for use, the presence of the needle forces parts of the spring clip into a position where these parts locks to the inside of the catheter hub, whereby movement of the spring clip relative the catheter hub is prevented. As the needle is withdrawn to a point where the tip passes these parts, the spring clip snaps into a position in which it is blocking access to the to the tip of the needle. Simultaneously, the part of the spring clip that previously locked to the inside of the catheter hub snap out of this position, whereby movement of the spring clip relative the catheter hub may occur. As the needle is further withdrawn, means are provided, e.g. a slot or a crimp on the needle, to lock the spring clip to the needle, whereby the spring clip is ejected from the catheter hub together with, and positioned on, the needle.

However, spring clips, like the type disclosed above, provide poor protection per se against drops of blood or body fluid that may move outwards from the interior of the catheter hub as the needle is removed. Such drops may, for example, spread infectious diseases.

There are various needle shields available which aim to shield not only the needle tip, but also the shaft of the needle as well after its withdrawal from the catheter tube. For instance, U.S. Pat. No. 6,379,332 discloses a needle protector assembly. To remove the needle shield assembly after it has served its purpose of arranging the catheter, the user holds the hub of the catheter with one hand and holds a slider between the finger and thumb of the other hand. The user then pulls the slider rearwardly along a housing so that the needle shaft is withdrawn from the shaft of the catheter. When the slider is pulled back to its full extent along the housing the needle assembly is unlocked from the catheter and the needle protector assembly covers the needle shaft and the needle tip.

Another example is EP1352668, which discloses a shielding protection device for needles. The needle assembly includes a needle cannula having a puncture tip at its distal end and a hub, which supports the needle cannula. A hollow outer shield co-axially surrounds a distal end of the hub and has an inner surface which is in cooperating engagement with an outer surface of the hub. The hub includes a first tab extending outwardly, and the outer shield includes a second tab. The first tab and the second tab are configured such that opposing forces applied against the tabs cause the outer shield to move from a retracted position in which the puncture tip of the needle cannula is exposed, to an extended position in which the outer shield covers the puncture tip.

A further example is disclosed in EP1389991, in which a catheter insertion device is provided for inserting an over-the-needle catheter. The device includes an insertion needle that is retractable into a housing of the device after use to prevent exposure to the contaminated needle. A needle retainer releasably retains the needle in an extended position against a rearward bias of a biasing element. The needle retainer engages a hub of the catheter so that when the catheter is removed from the insertion device, the needle retainer automatically releases the needle. The biasing element then propels the needle rearwardly into the housing of the device.

However, these shielding devices in turn also have several drawbacks, such as being cumbersome to use and having ungainly designs. In addition, they may require the use of two hands which is unsuitable since health care staff often need to do several tasks simultaneously.

Hence, an improved device for automatic shielding of the whole needle after its employment for introduction of a catheter tube is desired.

SUMMARY

It is an object of the present disclosure, considering the disadvantages mentioned above, to provide an improved device for automatic shielding of the whole needle after its employment for introduction of a catheter tube.

In a first aspect, there is provided a needle shielding device for a catheter instrument extending along a longitudinal axis A, comprising an inner part comprising an inner part track extending along said axis A, a middle part comprising a middle part track extending along the axis A, and an internal middle part engagement means, an outer grip part, comprising a needle hub, holding a needle extending along the axis A, and grip part internal engagement means. The grip part internal engagement means is configured to slidingly engage the middle part track, and the middle part engagement means is configured to slidingly engage the inner part track such that the inner part, the middle part and the grip part are telescopingly slidable in relation to one another. The needle shielding device, and the grip, middle and inner parts thereof, have a substantially rectangular lateral cross-section, and the inner part track and the middle part track are located along a corner of the rectangular lateral cross-section of the inner part and the middle part, respectively.

In a second aspect, there is provided a needle shielding device for a catheter instrument extending along a longitudinal axis A, comprising an inner part comprising an inner part track extending along the axis A, a middle part comprising a middle part track extending along the axis A, and an internal middle part engagement means, an outer grip part, comprising a needle hub, holding a needle extending along the axis A, and grip part internal engagement means. The grip part internal engagement means is configured to slidingly engage the middle part track, and the middle part engagement means is configured to slidingly engage the inner part track such that the inner part, the middle part and the grip part are telescopingly slidable in relation to one another. The middle part and the inner part each comprise a middle part groove and an inner part groove, respectively, wherein the grooves extend along the axis A and are arranged on a bottom surface, a top surface, a corner or a side surface of the middle part and inner part, respectively.

In a third aspect there is provided a needle shielding device for a catheter instrument extending along a longitudinal axis A, comprising an inner part comprising an inner part track extending along said axis A, a middle part comprising a middle part track extending along said axis A, and an internal middle part engagement means, an outer grip part, comprising a needle hub, holding a needle extending along said axis A, and grip part internal engagement means. The grip part internal engagement means is configured to slidingly engage the middle part track, and the middle part engagement means is configured to slidingly engage the inner part track such that the inner part, the middle part and the grip part are telescopingly slidable in relation to one another. The needle shielding device further comprises a needle tip shielding device arranged on a proximal end thereof. Preferably the needle tip shielding device is connected to an inner part proximal end, and the needle tip shielding device is protected by at least two edge blinkers arranged at the inner part proximal end.

In a fourth aspect, there is provided a needle shielding device for a catheter instrument extending along a longitudinal axis A, comprising an inner part comprising an inner part track extending along said axis A, a middle part comprising a middle part track extending along said axis A, and an internal middle part engagement means, an outer grip part, comprising a needle hub, holding a needle extending along said axis A, and grip part internal engagement means. The grip part internal engagement means is configured to slidingly engage the middle part track, and the middle part engagement means is configured to slidingly engage the inner part track such that the inner part, the middle part and the grip part are telescopingly slidable in relation to one another, and the inner part further comprises a push tab. Preferably the push tab is integrally formed with the inner part and an angle between a push tab upper surface and an upper push part is between 90 and 150 degrees. More preferable, the angle is between 100 and 130 degrees, most preferable about 110 to 120 degrees.

In a fifth aspect, there is provided a needle shielding device for a catheter instrument extending along a longitudinal axis A, comprising an inner part comprising an inner part track extending along the axis A, an outer grip part, comprising a needle hub, holding a needle extending along the axis A, and grip part internal engagement means. The grip part internal engagement means is configured to slidingly engage the inner part track, such that the inner part and the grip part are telescopingly slidable in relation to one another. During use, the grip part is slidingly movable along the inner part due to that a friction force between the grip part engagement means and the inner part track is smaller than a connecting force between the inner part and a catheter assembly, and the inner part further comprises inner part grip ribs on an upper external side thereof.

Further features of the disclosure and its embodiments are set forth in the appended claims.

BRIEF DESCRIPTION OF THE DRAWINGS

These and other aspects, features and advantages of which the disclosure is capable will be apparent and elucidated from the following description of non-limiting embodiments of the present disclosure, reference being made to the accompanying drawings, in which.

DETAILED DESCRIPTION OF THE EMBODIMENTS

Embodiments of the present disclosure will be described in more detail below with reference to the accompanying drawings in order for those skilled in the art to be able to carry out the disclosure. The disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. The embodiments do not limit the disclosure, but the disclosure is only limited by the appended patent claims. Furthermore, the terminology used in the detailed description of the particular embodiments illustrated in the accompanying drawings is not intended to be limiting of the disclosure.

Embodiments of the present disclosure will now be described below with reference to FIGS. 1 to 6.

Figure 1A:
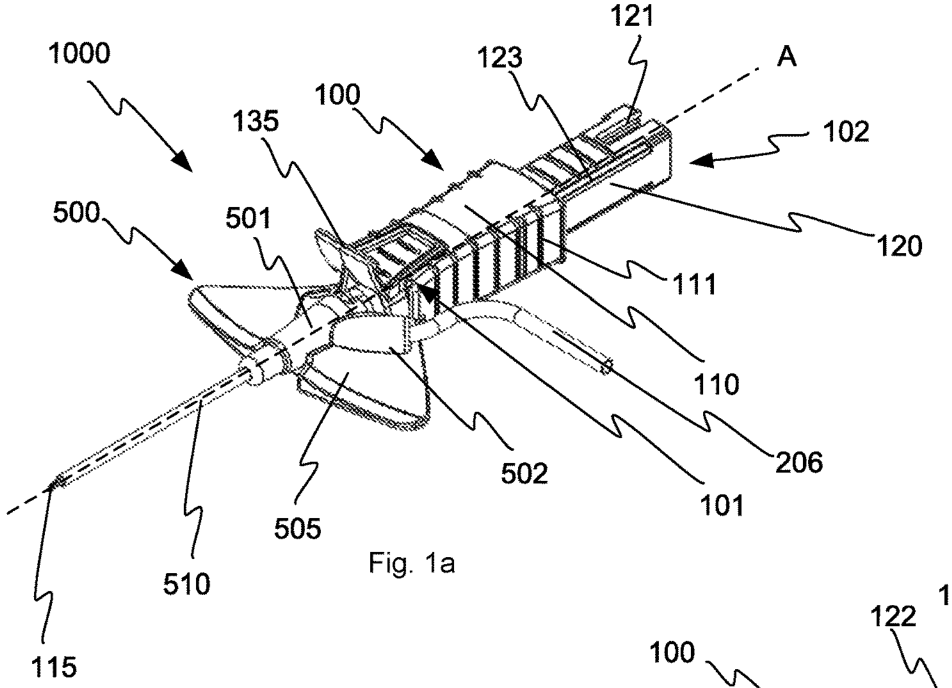
FIG. 1*a* is an isometric view of a catheter instrument having a needle shielding device in a retracted configuration.

Referring to FIG. 1*a*, there is provided a catheter instrument 1000 comprising a needle shielding device 100, also referred to as an encapsulation device 100 herein, and a catheter assembly 500. The catheter assembly 500 comprises a catheter hub 501, a coupling for an extension tube 502, a pair of wings 505 and a hollow catheter tube 510. The disclosed catheter assembly 500 is a closed system, i.e. a system wherein a septum is provided in the catheter hub 501, and fluids are withdrawn or introduced through a lateral extension tube 506. However, the needle shielding device 100 is equally applicable on an open catheter system, wherein fluid can be introduced or withdrawn longitudinally from a distal end of the catheter hub.

Figure 1B:
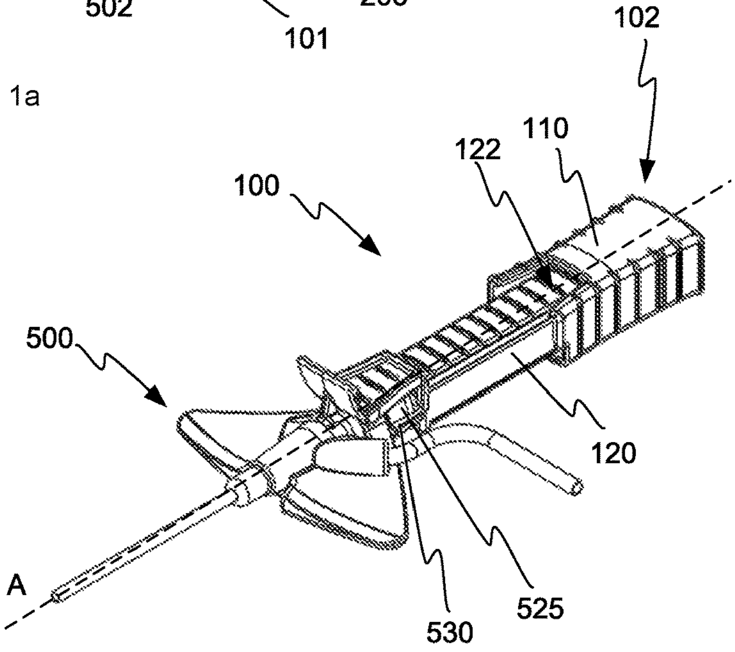
FIG. 1*b* is an isometric view of a catheter instrument with said needle shielding device in a partly extracted configuration.
Figure 1C:
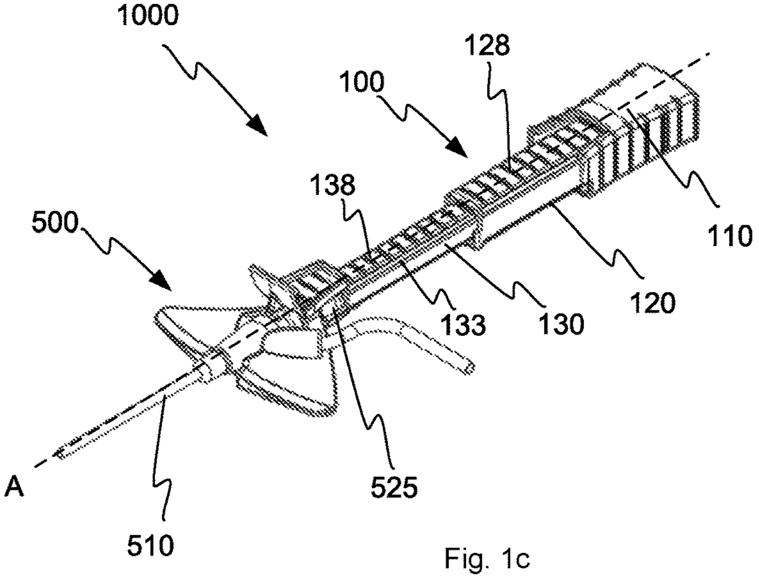
FIG. 1*c* is an isometric view of a catheter instrument with said needle shielding device in an extracted configuration.

The needle shielding device 100 disclosed herein is a telescopic encapsulation shielding assembly, having a retracted configuration, an intermediate configuration, in which the telescopic assembly is partly extracted, and a fully extracted configuration. The three configurations are shown in FIGS. 1*a* to 1*c*.

In FIG. 1*a*, the needle shielding device 100 is in its retracted configuration and extends along a longitudinal central axis A in a proximodistal direction. The needle shielding device 100 has a needle shield proximal end 101, facing towards the catheter tube 510 and an oppositely facing needle shield distal end 102.

A grip part 110 and a middle part 120 of the needle shield device 100 are also shown in FIG. 1*a*. The needle shielding device 100 is extracted by pulling the grip part 110 in a distal direction. The grip part 110 has a plurality of grip side surface ribs 111, which enhance grip properties for the user. The middle part 120 extends longitudinally from the distal end 102 towards the proximal end 101 along the axis A and has a middle part incision 121, extending longitudinally and opening up distally into the distal end 102 of the needle shielding device 100 and a middle part distal end 122.

The middle part 120 has a square like shape, and further comprises along each of its outer corner edges a longitudinal track 123, also referred to herein as a chamfer, configured to receive the grip part 110, which is slidingly movable along the longitudinal chamfers 123. The connection between the grip part 110 and the middle part 120 will be described more in detail with reference to FIGS. 2*a* and 2*b*. Further, the needle shielding device 100 comprises a push tab 135. The catheter tube 210 is hollow and houses a needle 115 in FIG. 1*a*.

FIG. 1*b* shows the telescopic needle shielding device 100 in its intermediate configuration. The grip part 110 is extracted to a middle part distal end 122. The middle part 120 covers and houses an inner part 130 (shown in FIG. 1*c*). As the grip part 110 is extracted, a connection portion 525 of the catheter assembly 500 is revealed. The connection portion 525 is provided with connection portion protrusions 230. The grip part 110 is releasably connected to the connection portion 525 of the catheter assembly 500. Further details of the connection between the grip part 110 and the connection portion 525 are described with reference to FIGS. 2*a* and 2*b*.

In FIG. 1*c*, the extracted configuration of the telescopic needle shielding device 100 is shown, which is still connected to the connection portion 525. The inner part 130 is exposed, and the push tab 135 is integral with the inner part 130. The middle part 120 has moved distally along the inner part 130. To enable the middle part 120 to slidingly engage and move along the inner part 130, the inner part 130 comprises longitudinal inner part tracks 133, also referred to as inner part chamfers herein.

Further, the middle part 120 and the inner part 130 are both provided with middle part grip ribs 128 and inner part grip ribs 138 on an upper external surface 126 of the middle part 120 and an upper external surface 139 of the inner part 130 respectively.

Grip Part

Figure 2A:
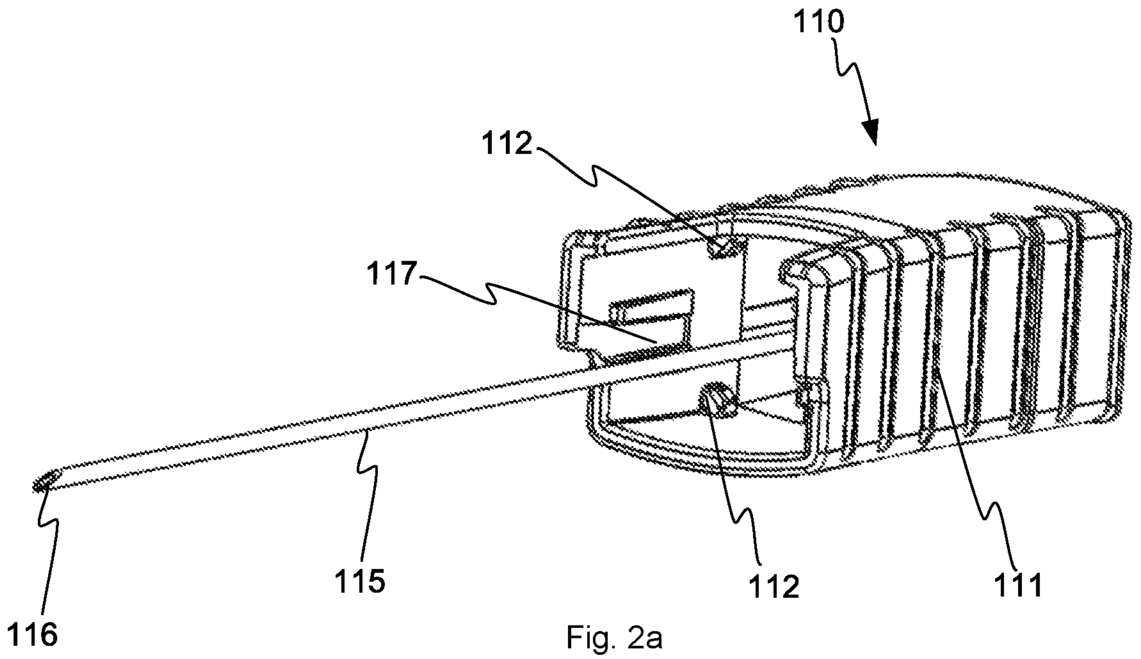
FIG. 2*a* is an isometric view of a grip part of needle shielding device comprising a needle.
Figure 2B:
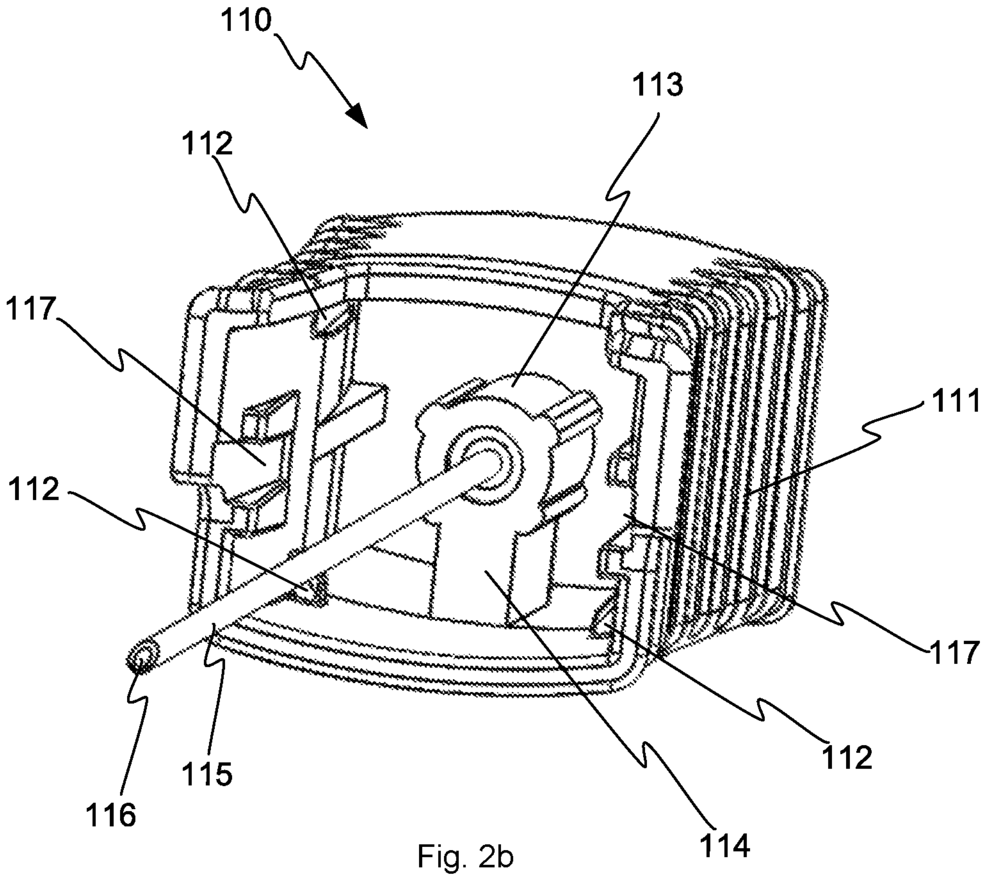
FIG. 2*b* is an isometric view of a grip part of the needle shielding device.

With reference to FIGS. 2*a* and 2*b*, the grip part 110 is shown in more detail. The grip part 110 holds a needle 115, extending longitudinally along the axis A, and comprises the grip side surface ribs 111. The needle 115 is equipped with a needle tip 116 at a proximal end of the needle 115. The distal end of the needle 115 is attached to the grip part 110.

Figure 3A:
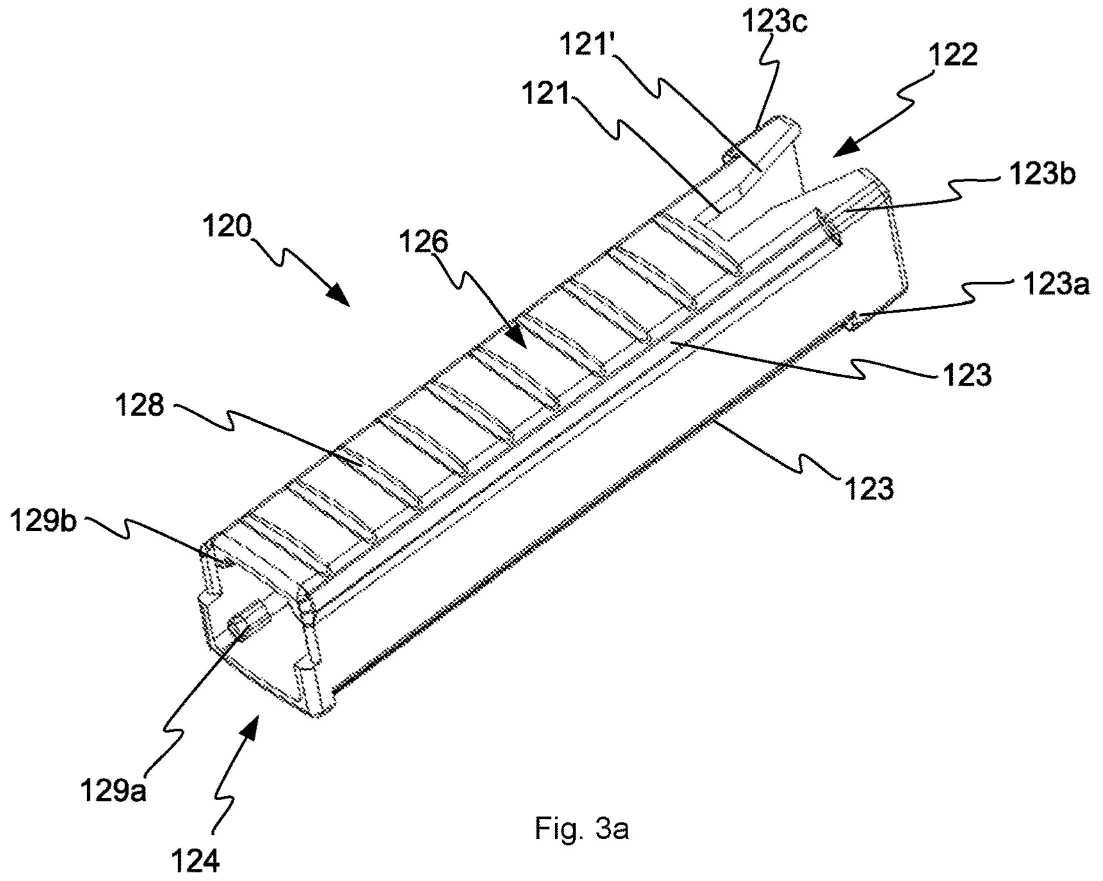
FIG. 3*a* is an isometric view of a middle part of the needle shielding device.

Further, in each grip part inner corner, there is provided a grip part inner protrusion 112, also referred to as a grip part connecting means herein, which is configured to engage and slide along the middle part tracks 123 (shown in FIG. 1*b* and FIG. 3*a*). The grip part 110 further comprises a needle hub 113 connected to the grip part 110 through an adapter part 114. A distal end of the needle 115 is connected to the needle hub 113 in an assembled state.

Further, as shown in FIGS. 2*a* and 2*b*, the grip part 110 comprises internal grip part engagement means, in the form of two grip part recesses 117, configured to engage the catheter assembly 500. However, the grip part engagement means 117 may be any suitable means which will fit with a catheter assembly known in the art.

When the grip part 110 is connected to the catheter assembly 500, each grip part recess 117 houses and engages a corresponding connection portion protrusion 530 on the connection portion 525. When a rearward force is applied to the grip part 110 by pulling it in a distal direction, the grip part recesses 117 will slide along the connection portion protrusions 530 until the grip part 110 is released from the connection portion 525. The connection portion 525 is arranged on a distal end of the catheter hub 501 of the catheter assembly 500.

The grip part 110 may further comprise a locking device (not shown) which prevents the re-use of the needle shielding device 100 and the possible exposure of the needle 115 after its use.

Middle Part

With reference to FIG. 3*a*, an isometric view of the middle part 120 is shown. The middle part 120 comprises the middle part incision 121, and the middle part tracks 123 as described above. Further, the middle part 120 comprises the middle part distal end 122 and a middle part proximal end 124. In addition, the middle part 120 has the upper external surface 126, provided with middle part grip ribs 128.

Similarly to the grip part 110, each proximal inner corner is equipped with a proximal internal middle part protrusion 129*a-d*, which when in an assembled configuration will engage the tracks 131 of the inner part 130. Only two of these protrusions 129*a*, 129*b* are seen in FIG. 3*a* due to the perspective of the figure. The middle part protrusions 129*a-d* are arranged at the middle part proximal end 124.

Further, as shown in FIG. 3*a*, the middle part tracks 123 do not extend all the way to the middle part distal end 122. As a result, there is provided distal middle part abutments 123*a*, 123*b*, 123*c*. The fourth and last corner not visible in FIG. 3*a* is also provided with a middle part abutment 123*d* (not shown). The middle part abutments 123*a-d* serve as stopping means for the grip part 110 when it is retracted and reaches the middle part distal end 122. Hence, when the grip part inner protrusions 112 will reach the abutments 123*a-d*, the grip part 110 will not be able to be retracted any further.

The middle part incision 121 shown in FIG. 3*a* allows the corners of the middle part 120 to flex inwardly toward the central axis A when the inner protrusions 112 of the grip part 110 must pass the abutments 123*a-d* during the assembly of the needle shielding device 100. In such case, the middle part 110 is assembled to the middle part 120 from the middle part distal end 122.

In addition, at the distal end 122 of the incision 121, in level with the distal part abutments 123*a-c*, the incision 121 has a tapered portion 121', such that the incision 121 is broadest at the distal end 122. The tapered portion 121' is useful when the grip part 110 is to be assembled to the middle part 120 from the middle part distal end 122. During this assembly, the grip part 110 must pass over the distal part abutments 123*a-d*, and hence there is a need for the ability for the distal end 122 of the middle part 120 to flex inwardly.

Figure 3B:
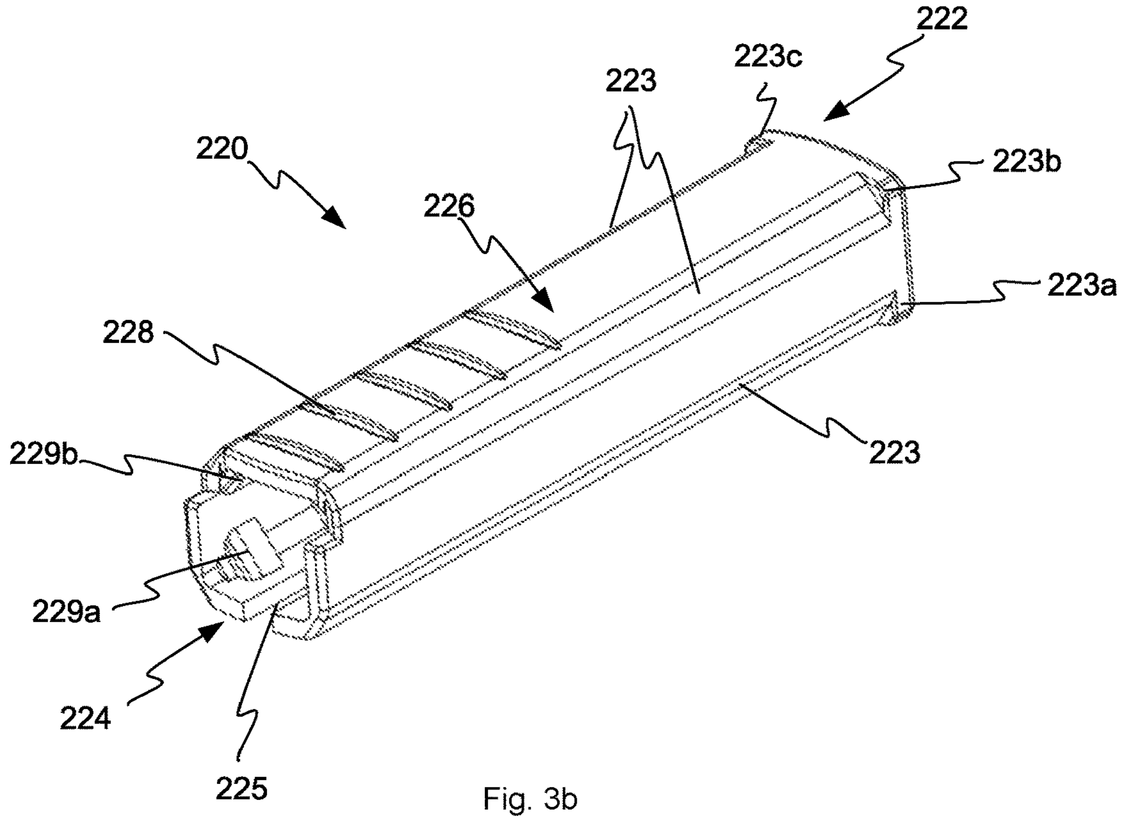
FIG. 3*b* is an isometric view of another middle part of the needle shielding device.

Another type of middle part 220 is shown in FIG. 3*b*. The middle part 220 has a middle part proximal end 224 and a middle part distal end 222. Similarly to the middle part 120 described with reference to FIG. 3*a*, the middle part 220 has a rectangular shape and is provided with a middle part track 223 in each longitudinal corner. At the distal end 222 thereof, each corner of the middle part 220 comprises an abutment 223*a-d* (abutment 223*d* is not shown in FIG. 3*b* as it is arranged on the bottom rear corner not visible in the figure).

A middle part groove 225 is arranged in and along a bottom surface of the middle part 220 and extends all the way to the middle part proximal end 224.

A middle part upper side 226 is equipped with a plurality of grip ribs 228. The middle part 220 may be equipped with more or less grip ribs 228 than shown in FIG. 3*b*.

The design of the middle part 220 allow for the assembling of the grip part 110 to the middle part 220 from the middle part proximal end 224. Hence, there is no need for a middle part incision 121 are provided on the middle part 120 in FIG. 3*a*. However, for such assembly to be possible, the middle part groove 225 is open at the middle part proximal end 224, as opposed to the middle part groove 125 shown in FIG. 3*a*, to make room for the adapter part 114 of the grip part 110.

Figure 4A:
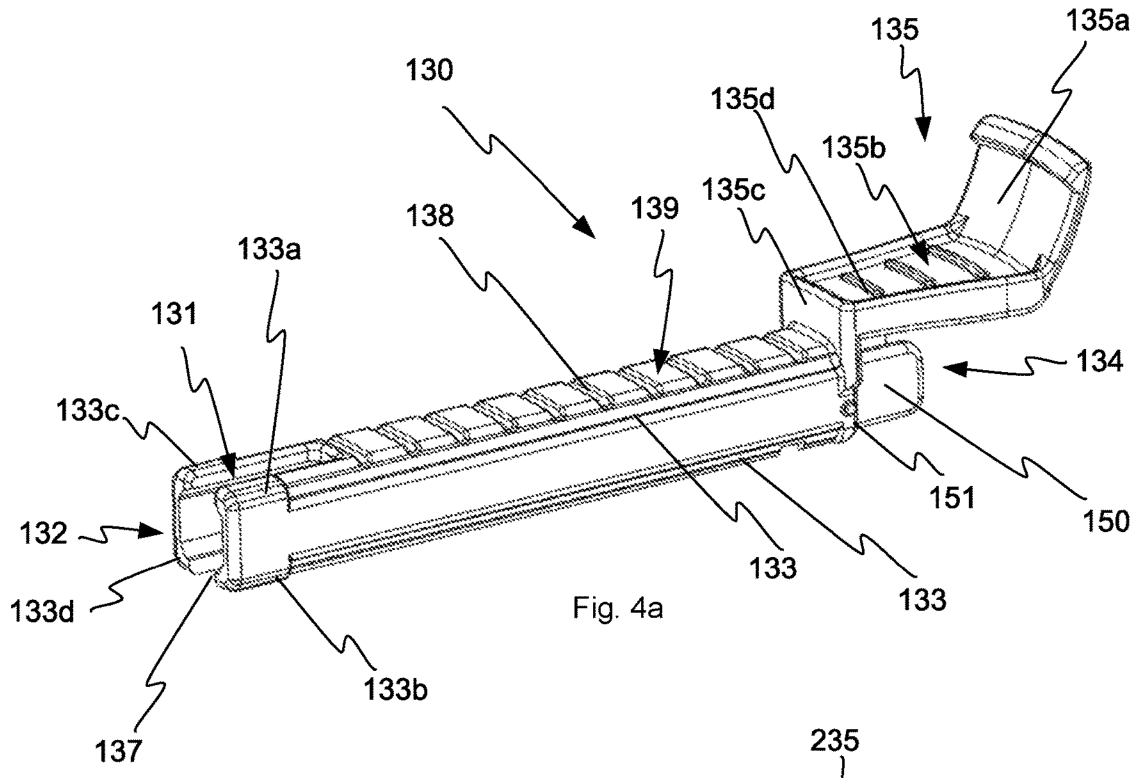
FIG. 4*a* is an isometric view of an inner part of the needle shielding device.

Hence, the middle part 120 shown in FIG. 3*a* is configured for snap fitting the grip part 110 onto the middle part 120 from a distal end 122 thereof, while the middle part 220 shown in FIG. 3*b* is configured for connecting the grip part 110 to the middle part 220 by threading the grip part 110 onto the middle part 220 from a proximal side 224 thereof Inner Part—Encapsulated Needle Tip The inner part 130 is shown in detail in FIG. 4*a*. The inner part 130 also extend along the axis A and may be provided with a needle tip shielding device 140, 240 (shown in FIGS. 5*a* and 5*b*) arranged at an inner part proximal end 134. An inner part distal end 132 is configured to face the middle part proximal end 124. Further, the inner part 130 has a plurality of inner part grip ribs 138, and inner part tracks 133 located at each lateral outer corner. The push tab 135 is integrally formed with the inner part 130 and further comprises a push tab upper surface 135*b* and provided with push tab grip ribs 135*d*.

Furthermore, the inner part 130 comprise an inner part incision 131 shown in FIG. 4*a*, which allows the corners of the inner part 130 to flex laterally inwardly toward the central axis A when the inner protrusions 129*a-d* of the middle part 120 must pass the abutments 133*a-d* to assemble the needle shielding device 100.

In addition, the inner part 130 is provided with a pair of blinkers 150 each extending proximally and longitudinally from an inner part proximal side edge 151. Said blinkers 150 encapsulate the needle tip clip 140. This in turn prevents blood drops from leaking out from the needle shielding device 100 and also hides the needle tip 116 (not shown) and makes it look less like a needle. An additional blinker may also be provided on the proximal bottom edge, opposite to the push tab (not shown).

The blinkers 150 form an inner part end 155, which is substantially square shaped in its lateral cross-section. The inner part end 155 has a mating configuration with the connection portion 225, which is hollow and houses the inner part end 155 when the needle shielding device 100 is connected to the catheter assembly 200.

Figure 4B:
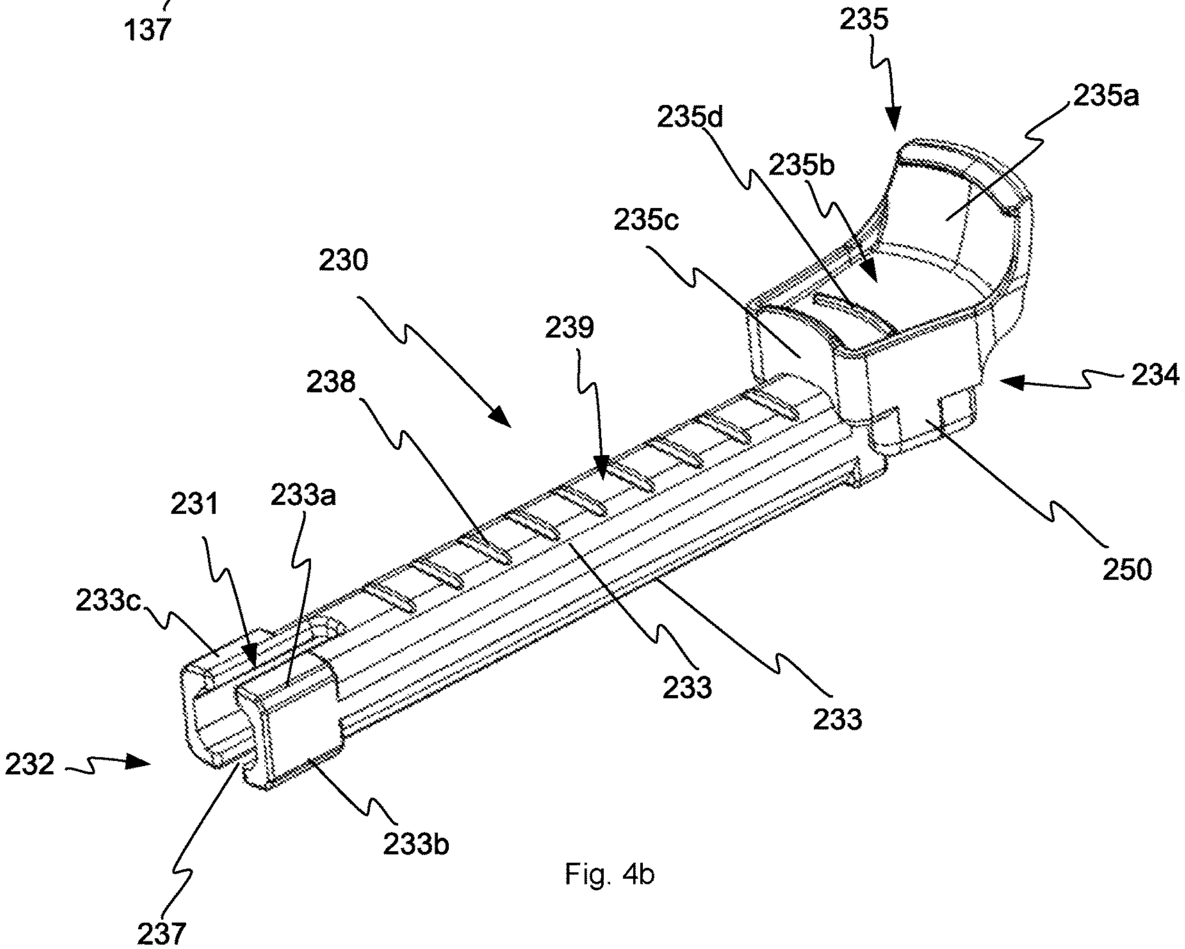
FIG. 4*b* is an isometric view of another inner part of the needle shielding device

With reference to FIG. 4*b*, an inner part 230 according to another embodiment is shown. The inner part 230 has an inner part distal end 232 and an inner part proximal end 234. An upper surface 239 is provided with a plurality of inner part grip ribs 238.

The proximal end 234 comprises a push tab 235 having a push tab upper surface 235*b* which is provided with a push tab grip rib 235*d*. A pair of blinkers 250 extends from the push tab 235. The details of the blinkers 250 will be explained in more detail with reference to the rotation securement and FIGS. 11*a* and 11*b*.

Figure 5A:
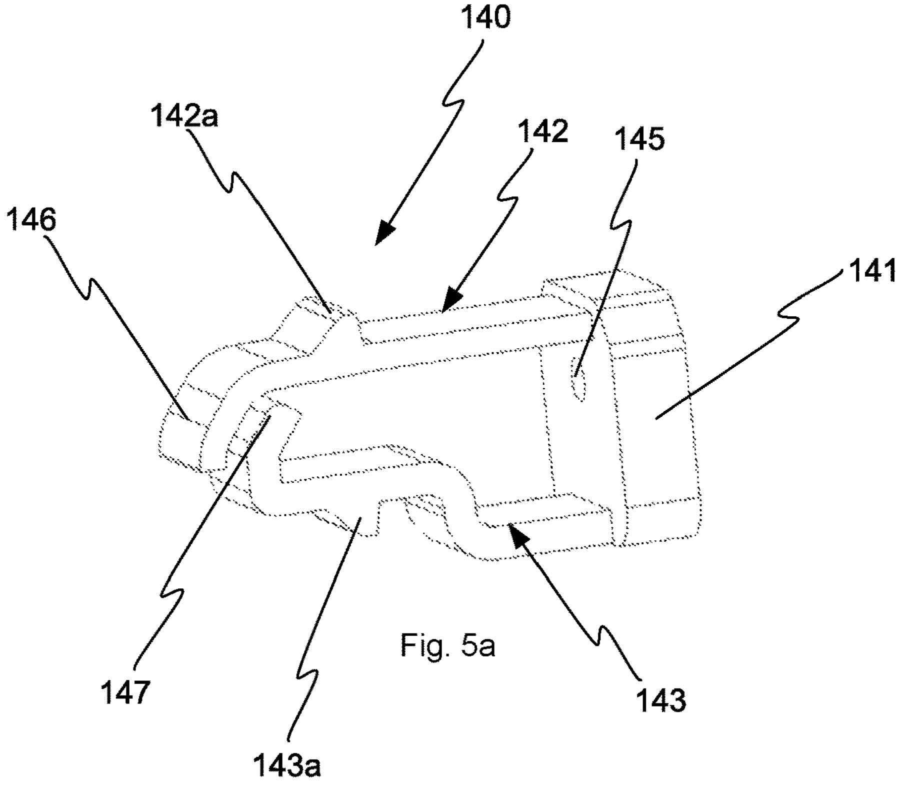
FIG. 5*a* is an isometric view of a needle tip shielding device.

FIG. 5*a* shows the needle tip shielding device 140 having a base 141, a bottom spring arm 142, a top spring arm 143 and an aperture 145 configured to receive a needle 115 (not shown). Each arm 142, 143 is provided with a trapezoidal protrusion 142*a*, 143*a* configured to engage the inside of the connection portion 225, and a top arm end 146 and bottom arm end 147 respectively.

The spring arms 142, 143 of the needle tip shielding device 140 in FIG. 5*a* are flexible. Hence, when the needle 115 (not shown) is assembled in the catheter instrument 1000 (as shown in FIG. 1*a*) the top arm end 146 and bottom arm end 147 are flexed away from the longitudinal axis A such that the arm ends 146, 147 enclose the shaft of the needle 115. When the needle 115 is extracted, it slides distally backwards in the aperture 145. When the needle tip 116 (not shown) passes the arm ends 146, 147, the top spring arm 142 and the bottom spring arm 143 will immediately flex inwardly toward the central axis A to attain the configuration shown in FIGS. 5*a* and 6*b*. In this state, the needle tip 116 will abut the inner side of the bottom spring arm end 147 is any attempt is performed to push the needle 115 in a proximal direction.

Figure 5B:
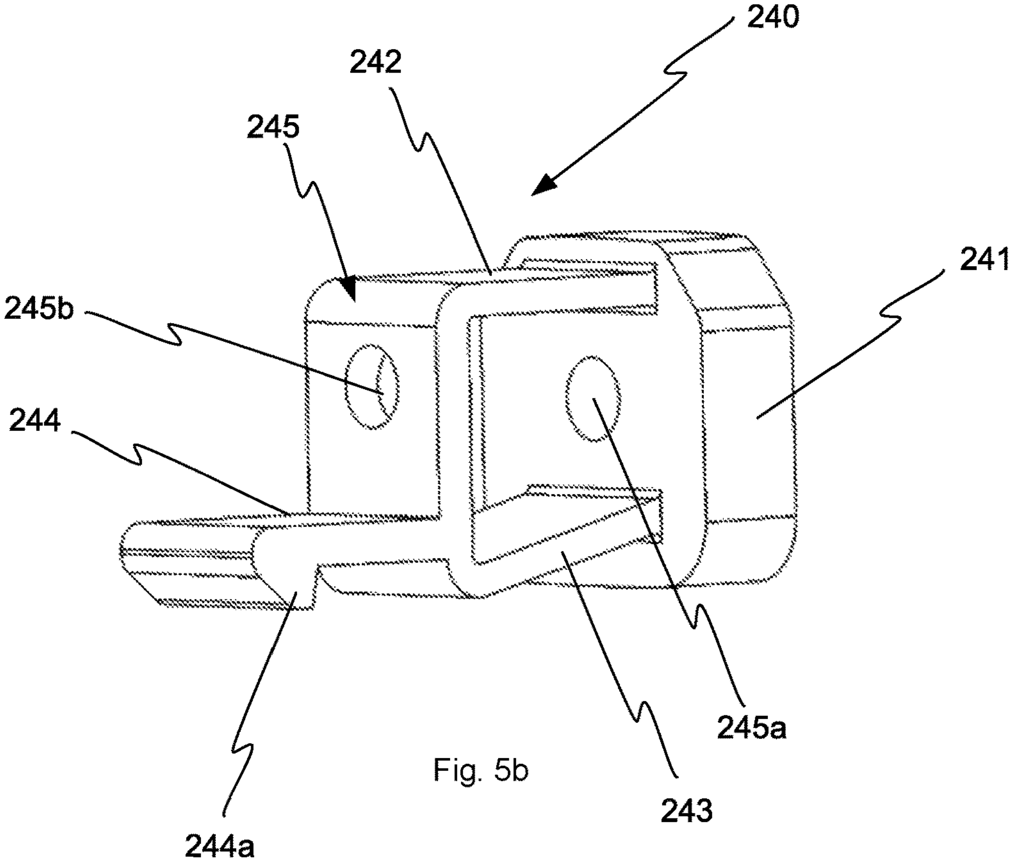
FIG. 5*b* is an isometric view of another needle tip shielding device.

A needle tip shielding clip 240 according to another embodiment is shown in FIG. 5*b*. The needle tip shielding clip 240 comprises a base 241, a first aperture 245*a* and a second aperture 245*b* and a needle clip housing 245. The housing 245 has an upper arm 242 and a bottom arm 243. An arm 244 extends from the housing 245 and in turn comprises a trapezoidal protrusion 244*a*, configured to engage the inside of the connection portion 225.

The first and second apertures 245*a*, 245*b* are configured to receive a needle 115 (not shown). The clip 240 in FIG. 4*b* is in its actuated locking state. When a needle 115 is inserted through the apertures 245*a*, 245*b*, the apertures 245*a*, 245*b* are forced into alignment with each other with respect to a lateral direction in relation to the axis A, as shown in FIG. 5*b*. Hence, the housing 245 is displaced upwards in FIG. 5*b*, and will flex into its default locking state when the needle 115 is retracted and passes the second aperture 245*b*. The bottom arm 243 will catch possible blood drops dripping from the needle 115.

Figure 5C:
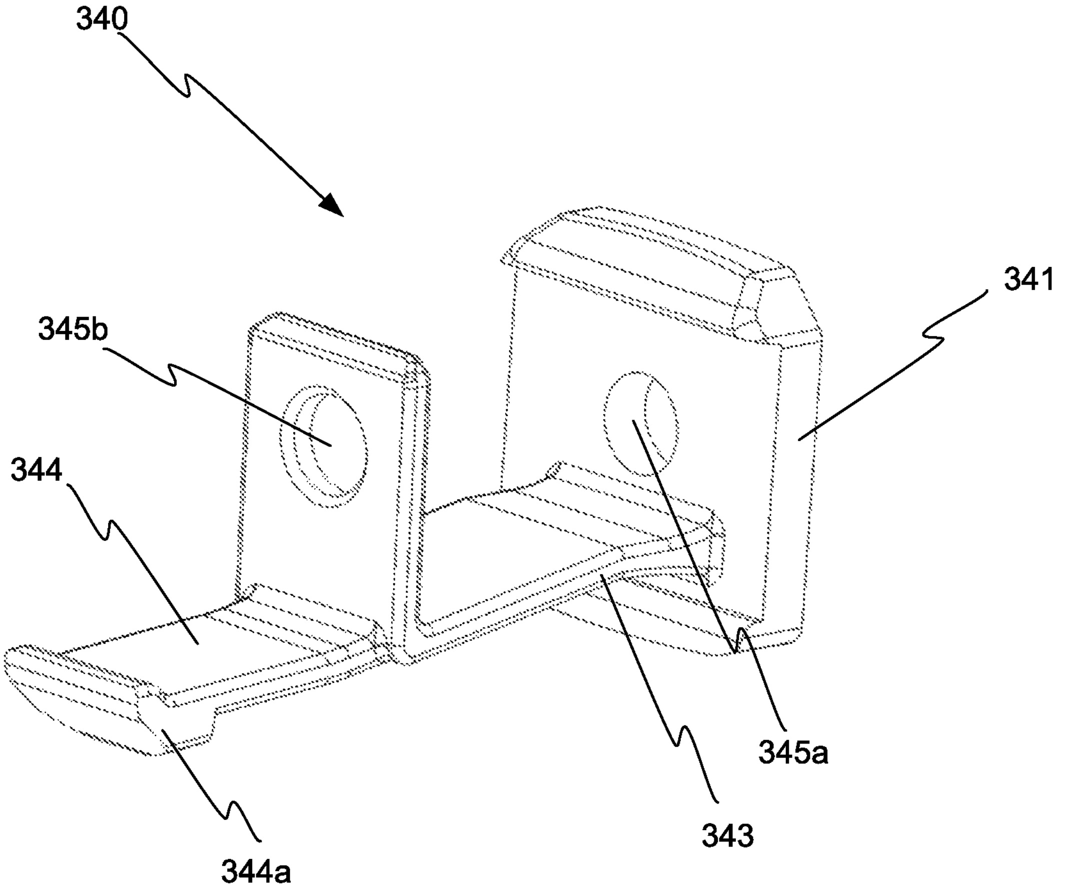
FIG. 5*c* is an isometric view of yet another needle tip shielding device.

The upper arm 242 is an optional feature. A needle tip shielding clip 340 according to a third embodiment is shown in FIG. 5*c*. The needle tip shielding clip 340 has a base 341, a first aperture 345*a* and a second aperture 345*b*. Further, it has a bottom spring arm 343. An additional arm 344 extends from the bottom arm 343 and comprises a trapezoidal protrusion 344*a*, configured to engage the inside of the connection portion 225. The needle 115 is to be held by the apertures 345*a*, 345*b*.

Further, the upper arm 242 may also be provided with a trapezoidal protrusion (not shown) configured to engage the inside of the connection portion 225. Preferably, the needle tip shielding clip 240 is combined with the inner part 230. The needle tip shielding devices 140, 240 may be formed integrally with the inner part 130, 230. In addition, the needle tip shielding device 240 may comprise additional arms on sides as well to prevent blood contamination.

Cross-Sectional Views (Lateral and Longitudinal)

Figure 6A:
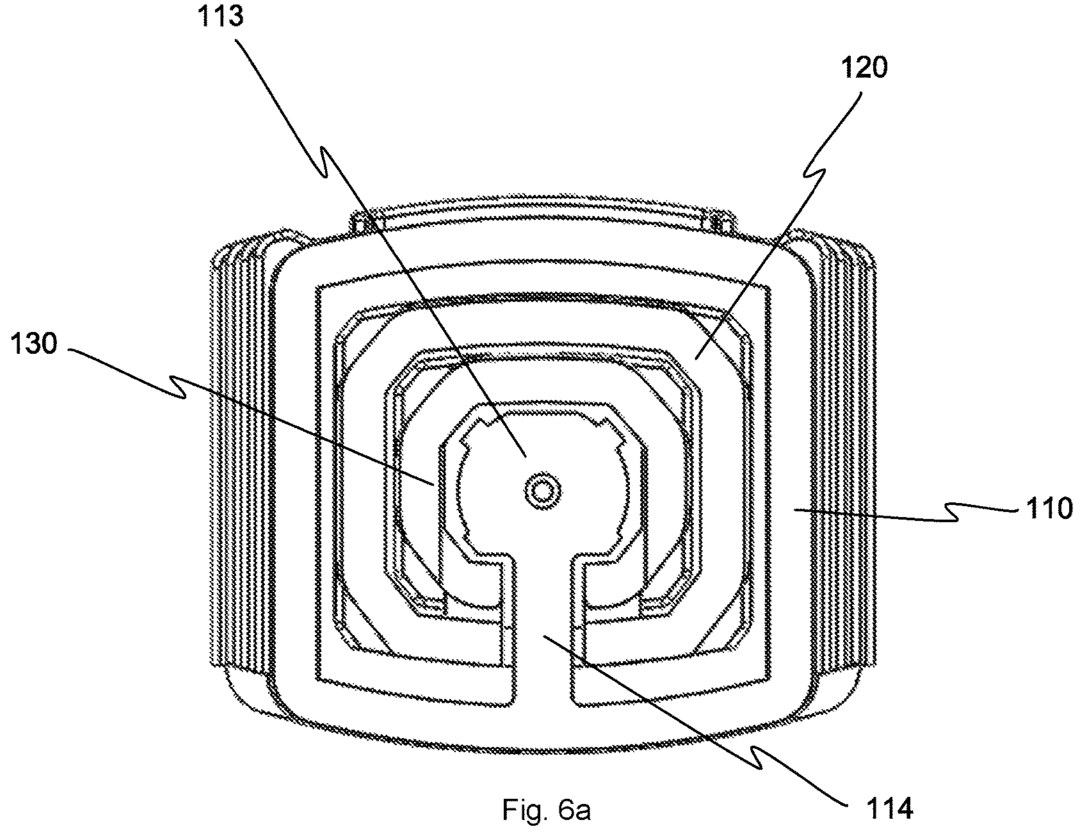
FIG. 6*a* is a lateral cross section of a needle shielding device in a retracted configuration.

As shown in FIG. 6*a*, a lateral cross-section of the retracted telescopic needle shield assembly 100 is substantially square shaped. A substantially rectangular or square lateral cross-section prevents rotation between the telescopic grip part 110, middle part 120 and inner part 130. In addition, said rectangular shape gives controlled motion of the device 100. Further, the combination of the rectangular shape and that a middle part groove 125 extends longitudinally while keeping a portion of the middle part proximal end 124 intact, the corners of the proximal middle part end 124 prevent the corners to flex.

In FIG. 6*a*, the adapter part 114, which binds the needle hub 113 and grip part 110 together, is arranged such that it coincides with the inner part groove 137 and the middle part groove 125. In order to assemble the grip part 110 to the telescopic middle part 120, the abutments 123*a*, 123*b* need to flex inwards. However, the middle part 120 has no space to flex inwards, since it conflicts with the adapter part 114 that fills out the middle part groove 125 where the distal abutments 123*a*, 123*b* should flex inwards.

Figure 6B:
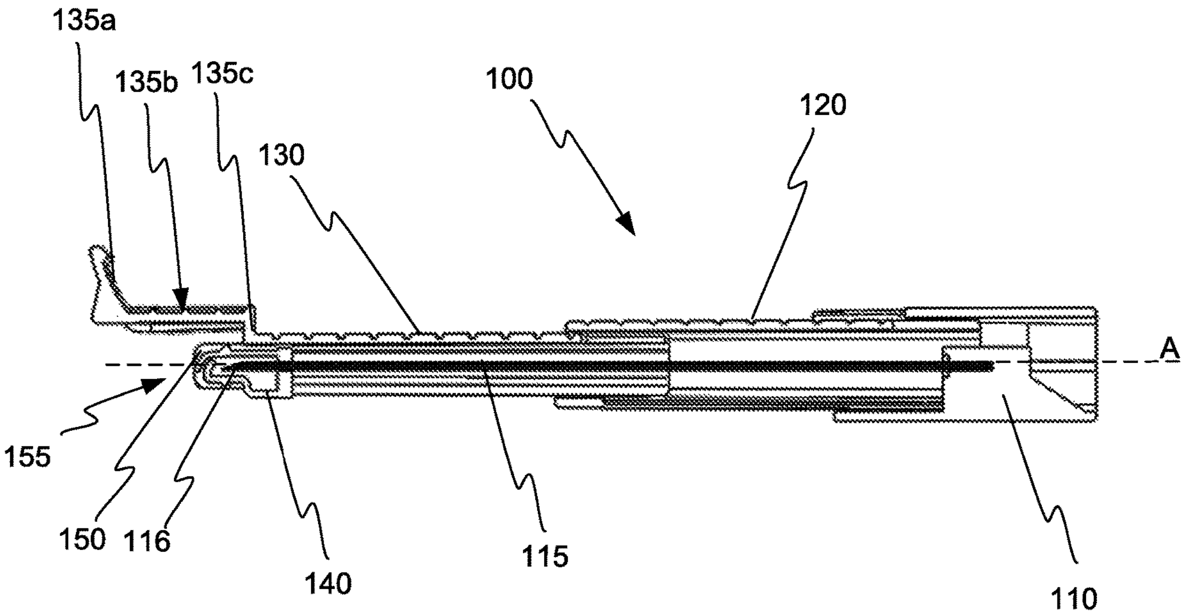
FIG. 6*b* is a longitudinal cross section of the a needle shielding device in an extracted configuration.

With reference to FIG. 6*b*, a longitudinal cross-section of the needle shielding device 100 extending along the central axis A is shown. The needle shielding device 100 has been released from the catheter assembly 200 and is shown in its extracted configuration, where the needle shielding device 100 encapsulates the needle 115 entirely. At the inner part end 155, the needle tip shielding device 140 prevents the needle tip 116 from being exposed.

Push Tab

With reference to FIGS. 4*a*, 4*b* and 6*b*, details of the push tab area will now be further explained. The push tab 135, 235 has both an upper push part 135*a*, 235*a*, having a height of about 4 to 10 mm, preferably about 7 mm from an upper surface of the catheter assembly 200. An angle between a push tab upper surface 135*b*, 235*b* and the upper push part 135*a*, 235*a* is about between 90 and 150 degrees, such as between 100 and 130 degrees, preferably about 115 degrees. Further, the push tab 135, 235 comprises a rear push tab part 135*c*, 235*c*, which is approximately a finger tip length (about between 6 and 20, such as between 8 and 15 mm) behind the upper push part 135*a*, 235*a* and has a height lower than the upper push part 135*a*, 235*a* such as about 2 mm. In addition the push tab 135, 235 is provided with push tab rib(s) 135*d*, 235*d* on an upper surface 135*b*, 235*b* thereof. These features facilitates a good grip and precision at the insertion, and offers a good push point for the finger when the grip part 110 is retracted.

Figure 11A:
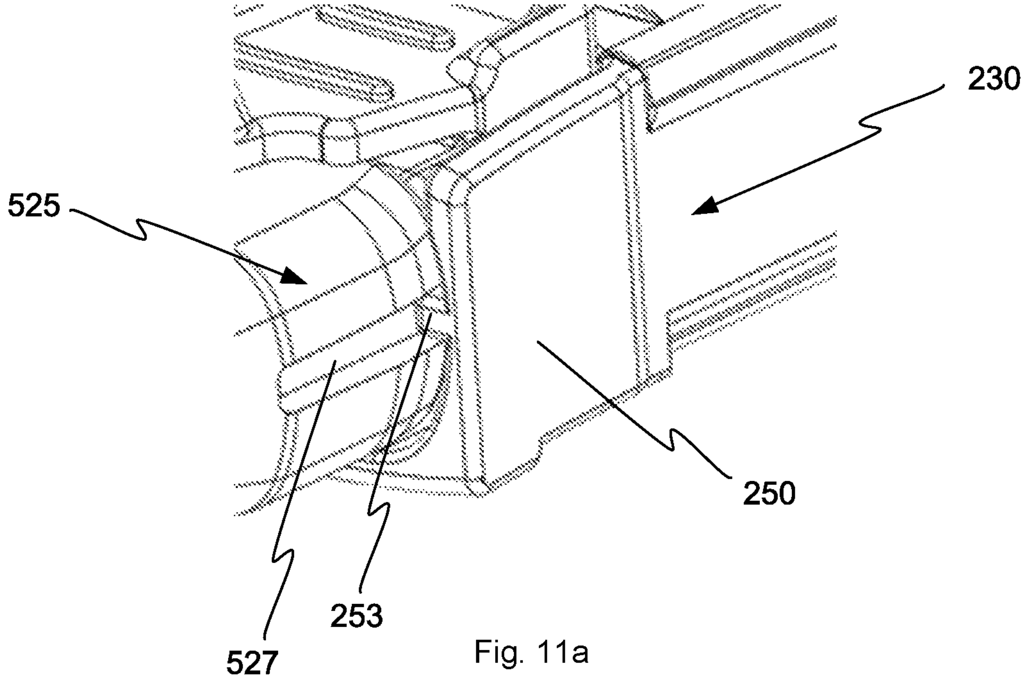
FIGS. 11*a* and 11*b* show rotational securements between the telescopic needle shielding device and a catheter assembly.
Figure 11B:
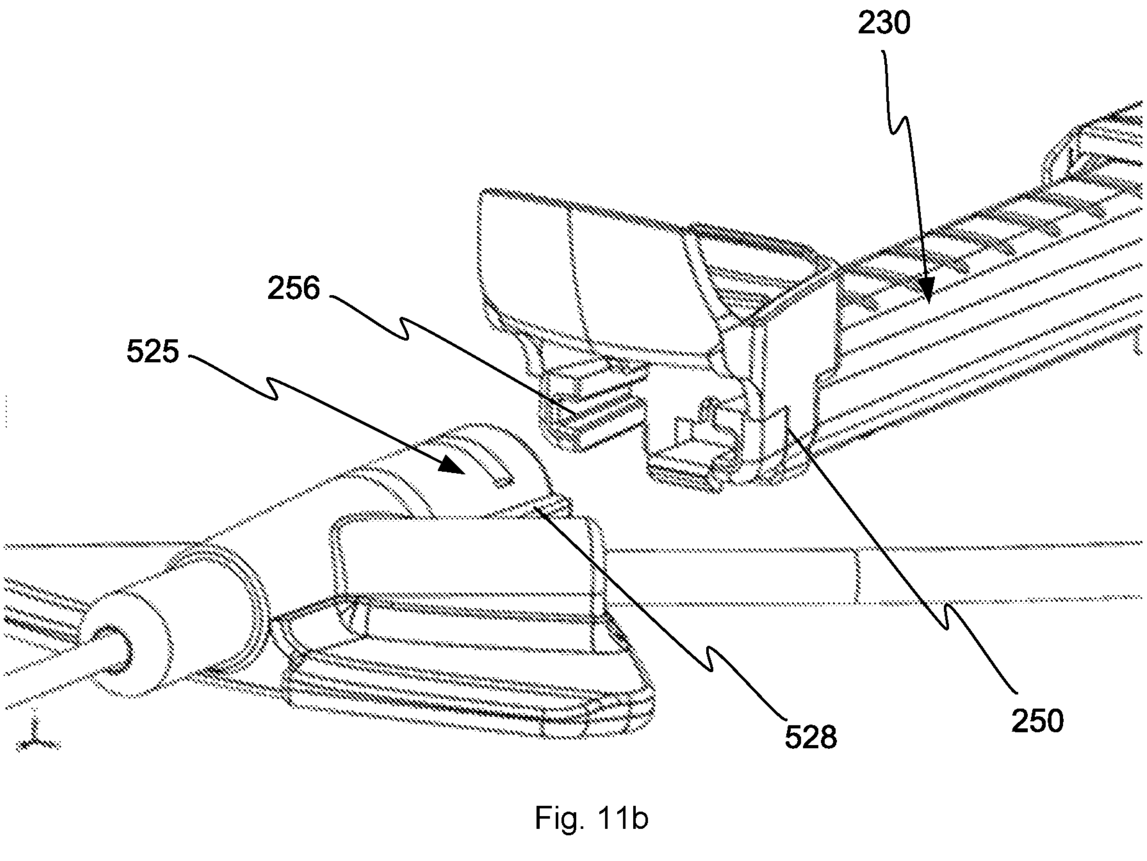

In addition, as mentioned with reference to FIG. 4*b*, the push tab 235 of the inner part 230 is provided with a pair of blinkers 250 which are described more with reference to FIGS. 11*a* and 11*b*.

Use of Telescopic Device

The function and use of the needle shielding device 100 disclosed herein will now be described in more detail with reference to FIGS. 1*a*-1*c*. The user holds the grip side surface ribs 111 of the grip part 110 and pushes the grip part 110 rearwardly with the aid of the push tab 135, 235. The grip part recesses 117 of the grip part 110 are released from the connection portion protrusions 530 of the connection portion 525. The grip part inner protrusions 112 (shown in FIGS. 2*a* and 2*b*) engage and slide along the middle part tracks 123, 223 until the grip part 110 reaches the distal end 122, 222 of the middle part 120, 220, as shown in FIG. 1*b*. The grip part inner protrusions 112 have then reached the abutments 123*a-d*, 223*a-d* and the grip part 110 is prevented from being released from the middle part 120, 220 since the abutments 123*a-d*, 223*a-d* act as stopping means for the grip part inner protrusions 112. Each grip part inner protrusion 112 will engage a corresponding abutment 123*a-d*, 223*a-d*.

When the user continues to pull the grip part 110 rearwardly, the user may take advantage of the grip ribs 128, 138, 228, 238 of the middle part 120, 220 and inner part 130, 230 to facilitate the use of the needle shielding device 100 with one hand. The grip part 110 is still connected to the middle part 120, 220 and further pulling of the grip part 110 in a distal direction will cause the middle part 120, 220 to start to telescopingly slide along the inner part tracks 133, 233. When the middle part inner protrusions 129*a-d*, 229*a-d* reach the inner part abutments 133*a-d*, 233*a-d* the needle tip 116 has passed the top and bottom spring arms 142, 143, 242, 243 and the needle tip shielding device 140, 240 is actuated. The inner part proximal end 134, 234 will upon further distal pulling of the needle shielding device 100 be released from the connection portion 525. The needle 115 is completely encapsulated (as shown in FIG. 6*b*) and both patient and clinician are protected from the needle tip 116.

Figure 10:
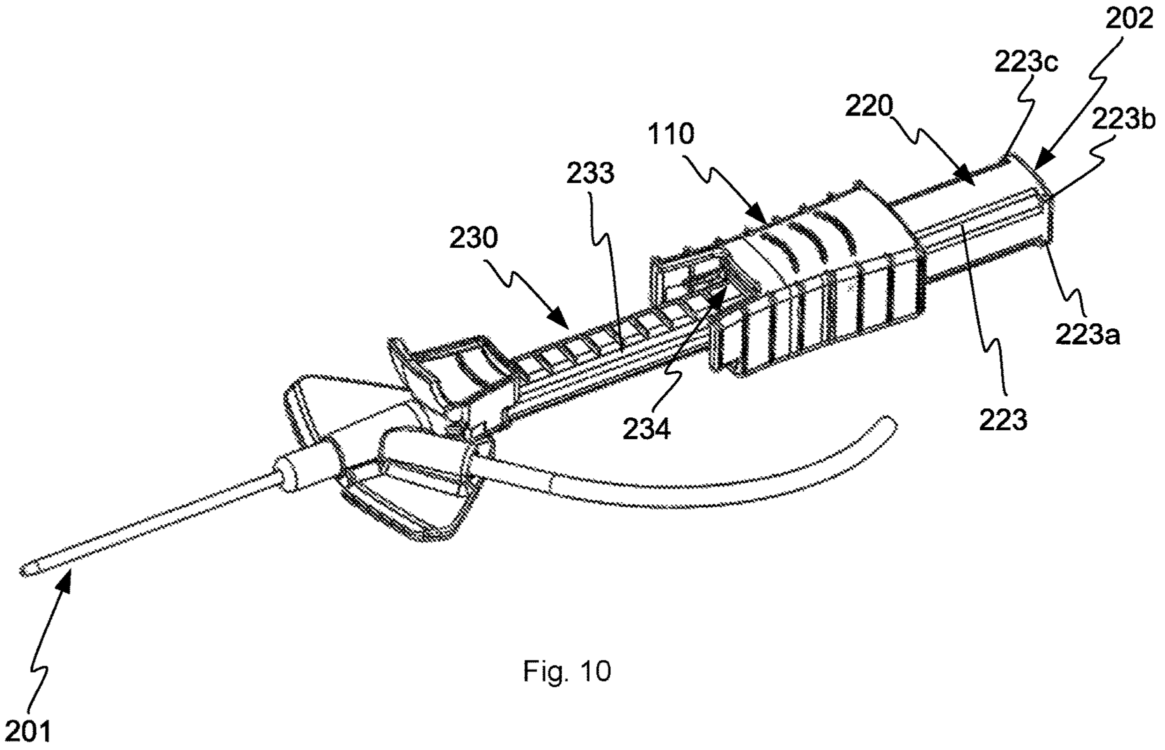
FIG. 10 is an isometric view of a telescopic needle shielding device.

Alternatively, the movement of the telescopic parts 110, 220, 230 will occur as shown in FIG. 10, where the grip part 110 and the middle part 220 first are fixed relative one another, while the middle part 220 slides along the inner part tracks 233. When the middle part 220 reaches the inner part distal end 234, the middle part inner protrusions 229*a-d* engage the inner part abutments 233*a-d* (not shown), whereby the grip part 110 continues to slide along the middle part tracks 223 until the grip part inner protrusions 112 reaches the middle part abutments 223*a-d*. Finally, the needle shielding device 100 will be released from the connection portion 525 of the catheter assembly 500.

The different middle parts 120, 220, and inner parts 130, 230 may be combined with each other and the grip part 110. The alternative movement described above may be applied also to the middle part 120 and the inner part 130.

Two Parts Moving at the Same Time Configuration

The friction and engaging force between the middle part inner protrusions 129*a-d*, 229*a-d* and the inner part tracks 133, 233 is smaller than the connection force between the needle shielding device 100 and the connection portion 525. The connection and rotation locking between the needle shielding device 100 and the connection portion 525 will be explained further below.

This relation between the connection force between the needle shielding device 100 and the catheter assembly 500 ensures that the grip part 110 and the middle part 120, 220 is allowed to slide telescopingly along the inner part 130, 230 so that the needle shielding device 100 reaches its extracted configuration before it is released from the catheter assembly 500.

The force relation between the parts 110, 120, 130 and the connection portion 225 enables a configuration where only two of the three parts 110, 120, 130 of the needle shielding device 100 will move in relation to each other at the same time. Optionally, the grip part 110, and the middle part 120, 220 will slide simultaneously along the middle part 120, 220 or the inner part 130, 230, respectively.

In the movement sequence shown with reference to FIGS. 1*a*-1*c*, the grip part 110 is released from the connection portion 525 first, and the inner part 130 will be connected to the connection portion 525 until the middle part 120 has reached the inner part distal end 132. Firstly, the grip part 110 will slide along the middle part 120 until the grip part reaches the middle part distal end 122. Secondly, the middle part 120 will move along the inner part 130 until the middle part 120 reaches the inner part distal end 132. Finally, the inner part 130 is released from the catheter assembly 500.

In FIG. 1*c*, the middle part 120 has slide along the inner part chamfers 133 and has reached the distal end 132 of the inner part 130. If the user continues to pull the needle shielding device 100 distally, the inner part 130 is released from catheter assembly 200 and the needle 115 (shown in FIGS. 1*a*, 2*a* and 2*b*) is encapsulated in its entirety in the extracted telescopic needle shielding device 100 as shown in FIG. 6*b*.

In the movement sequence shown in FIG. 10, the friction and engaging force between the middle part 220 and the inner part 110 is larger than the friction and engaging force between the middle part 220 and the inner part 230. Hence, the middle part 220 and the grip part 110 will not move relative one another while the middle part inner protrusions 229*a-d* engage and slide along the inner part tracks 233.

When the needle shielding device 100 has reached its extracted configuration, the inner part proximal end 134, 234 shall let go easily such that the patient will not experience an unpleasant feeling when extracting the needle from the catheter device 1000. The force needed shall not disturb the user. If felt, it shall only be an indication of where in the movement the needle 115 is.

Locking Mechanism Between the Telescopic Parts

Figure 8:
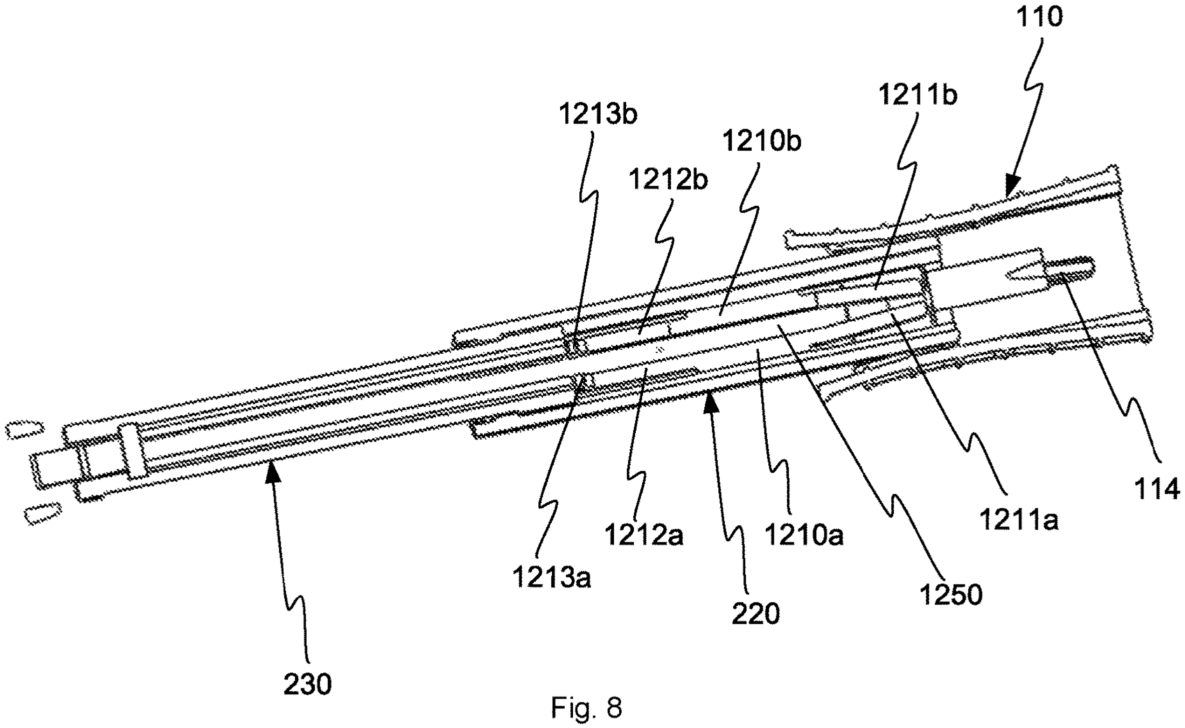
FIG. 8 is a perspective view of a bottom of a middle part comprising a locking mechanism.

The telescopic parts 110, 120, 220, 130, 230 may comprise locking mechanisms to ensure that the grip part 110 and the middle part 120, 220 cannot be moved towards the proximal end 101, 201 after the respective part 110, 220 has been extracted. FIG. 8 shows a bottom portion of a middle part 220 having two longitudinal locking ribs 1210*a*, 1210*b* extending in a proximodistal direction arranged such that a space 1250 is obtained between them. The grip part 110, the middle part 220 and the inner part 230 are in their extracted configuration in FIG. 8.

Each locking rib 1210*a*, 1210*b* has a flexible locking rib distal end 1211*a*, 1211*b*, and a flexible locking rib proximal end 1212*a*, 1212*b*. The locking rib distal ends 1211*a*, 1211*b* are both inclined laterally towards the central axis A, and the locking rib proximal ends 1212*a*, 1212*b* each comprise a laterally extending hook portion 1213*a*, 1213*b*.

When the grip part 110 telescopingly slides along the middle part 220, the adapter part 114 of the grip part 110 lies in the space 1250 between each locking rib 1210*a*, 1210*b*. In FIG. 8, the grip part 110 has been retracted to the middle part distal end 222 and thus, the adapter part 114 has slide out of the space 1250 and is being hindered from being moved towards the middle part proximal end 224 due to that the locking rib distal ends 1211*a*, 1211*b* have flexed laterally towards the longitudinal axis A to a resting state. Hence, the distance between the locking rib distal ends 1211*a*, 1211*b* in the locking state is too narrow for the adapter part 114. Therefore, the adapter part 114 cannot enter the space 1250.

Figure 9:
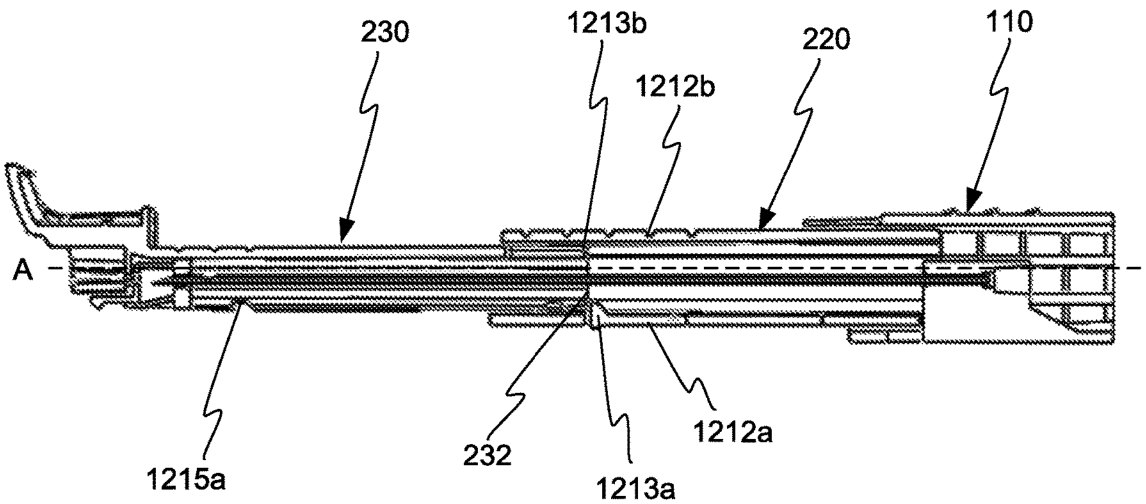
FIG. 9 is a side view of a needle shielding device.

The locking mechanism related to the locking rib proximal ends 1212*a*, 1212*b* each comprising a laterally extending hook portion 1213*a*, 1213*b* will now be explained with reference to FIG. 9. The inner part 230 comprises locking hook portion recesses 1215*a*, 1215*b* each configured to engage a respective laterally extending hook portion 1213*a*, 1213*b*. The locking hook portion recess 1215*b* is not shown in FIG. 9 since the figure is shown from the side. The hook portion 1213*a* in FIG. 9 is shown in its actuated state, being engage in the locking hook portion recess 1215*a*. When the middle part 220 has been retracted along the inner part 230, the hook portion 1213*a* will snap back to its locking state, thus flexing laterally towards the longitudinal centre axis A. The hook portion 1213*a* will then abut the inner part distal end 232 and cannot therefor no longer be moved in a proximal direction.

Preferably, the above described locking mechanisms yield a snapping sound, ensuring the user of the actuation of the locking state. The locking mechanisms should be firm enough to ensure secure locking, yet not cause unnecessarily high friction between the locking ribs 1210*a*, 1210*b* and the inner part 230 or middle part 220, which may cause discomfort for the patient.

The locking mechanisms allow for secure needle shielding even without a needle clip 140, 240 since the telescopic parts 110, 120, 220, 130, 230 are locked in relation to one another.

The locking mechanisms described may also be arranged in and applied to the middle part 120 as shown in FIG. 3*a* and the inner part 130 shown in FIG. 4*a*.

Grip Track in Encapsulation

Figure 7:
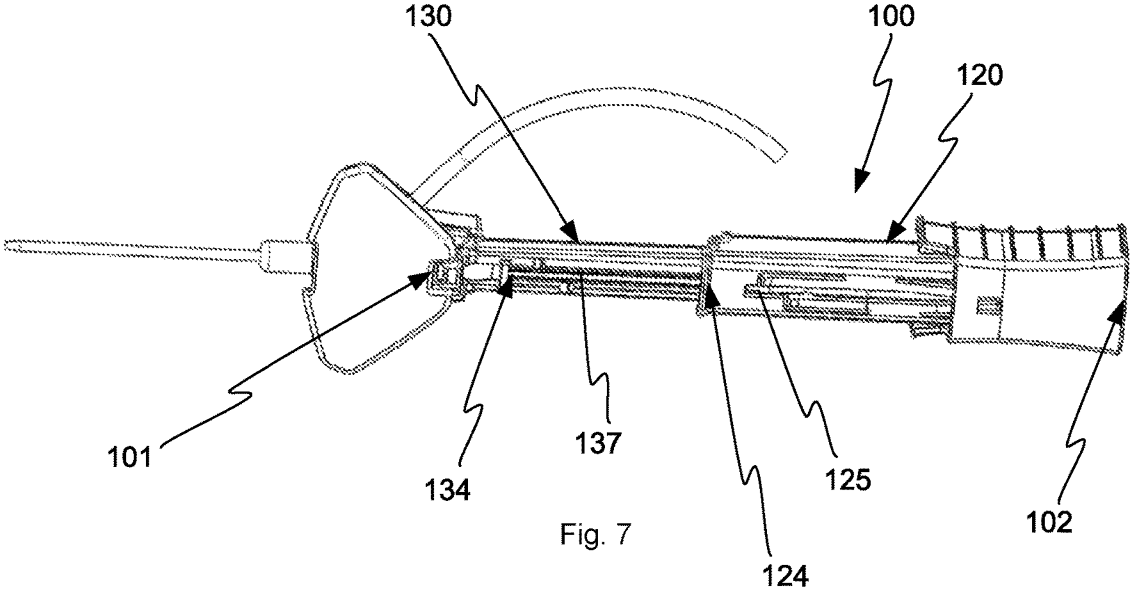
FIG. 7 is an isometric view of the catheter instrument as seen from below.

With reference to FIG. 7, a perspective view of the needle shielding device 100 from below is shown. Both the middle part 120 and the inner part 130 comprise a groove, being a middle part groove 125 and an inner part groove 137, respectively, which both extend longitudinally along the axis A, from the distal end 102 towards the proximal end 101. The middle part groove 125 and inner part groove 137 fit the adapter part 114 (not shown) when the grip part 110 slides rearwardly along the middle part 120 and the inner part 130.

The middle part groove 125 and the inner part groove 137 extends from middle part and inner part distal ends 122, 132 towards middle part and inner part proximal ends 124, 134. However, in FIG. 3*a* the groove 125 does not extend fully all the way to the proximal end 124 of the middle part 120. Hence, at least one proximal portion of the middle part 120 is circumferentially intact, as shown in FIG. 7. In FIG. 3*b*, the middle part groove 235 extends all the way from the middle part proximal end 224. The middle parts groove 125, 225 may also extend fully all the way from the middle part proximal end 124, 224 to the middle part distal end 122, 222.

Furthermore, the middle part groove 125 and the inner part groove 137 are in FIG. 7 arranged at the bottom side of the middle part 120 and inner part 130 respectively. This arrangement prevents blood splatter from the telescoping needle shielding device 100 and also causes the guidance of the needle 115, through the grip part 110, to be centric.

However, the grooves 125, 137 may also be arranged on the upper surface 126, 139 of the middle and inner parts 120, 130 respectively. This arrangement is designed to collect blood drops and prevent blood from flowing out from the telescoping needle shielding device 100. It also causes the guidance of the needle 115, through the grip part 110, to be centric. In this configuration, an adapter part of the grip part 110 will be arranged from the top side of the grip part 110 such that the adapter runs in the grooves 125, 137 arranges on top side of the middle and inner parts 120, 130 respectively.

In another embodiment, the grooves 125, 137 may be arranged on any one of the side surfaces of the middle part 120 or the inner part 130 respectively. This arrangement is designed to collect blood drops and prevent blood from flowing out from the telescoping needle shielding device 100, and prevents blood splatter. In this configuration, an adapter part of the grip part 110 will be arranged from the side surface(s) of the grip part 110 such that the adapter runs in the grooves 125, 137 arranges in the side surfaces of the middle and inner parts 120, 130 respectively.

A telescopic needle shield device of another embodiment may have fewer or more parts than the exemplary embodiment shown in FIGS. 1*a* to 1*c*, such as two parts or four, five or six parts. The tracks of the various parts may be of another shape than shown in the figures disclosed herein. Said engagement means which are slidingly movable within said tracks may also be of other shapes than disclosed herein.

Rotational Securement Between Telescopic Needle Shielding Device and Catheter Assembly & Rectangular Cross Section The grip part 110, the middle part 120, 220 and the inner part 130, 230 have a substantially rectangular lateral cross section. Due to this shape, it is advantageous to provide the inner part tracks 133, 233 and the middle part tracks 123, 223 along the corners of the extension of the inner part 130, 230 and middle part 120, 220, respectively. This is due to that the corners of each respective rectangular cuboid comprises more material than side walls of the middle part 120, 220 and the inner part 130, 230, rendering the corners to have a larger thickness than each side wall thereof.

The connection and rotational securement between the needle shielding device 100 and the catheter assembly 500 may be designed and function in different ways.

The connecting between the connection portion 525 of the catheter assembly 500 and the inner part 130 is created by the trapezoidal projections 142*a*, 143*a* (shown in FIG. 5*a*) and mating recesses on the internal surface of the connection portion 525, and by that the circumference of the inner part end 155 (shown in FIG. 6*b*) formed by the blinkers 150 correspond and fit into the connection portion 525. Furthermore, the inner part end 155 and the cavity of the connection portion 525 configured to receive said inner part end 155 both have a substantially square or rectangular lateral cross-section. Hence, this also prevents the needle shielding device 100 from rotating about the axis A in relation to the catheter assembly 500.

Alternatively, the inner part proximal end 234 has a rectangular shape, and surrounds the connection portion 525 also having a rectangular shape, thus preventing unwanted rotation between the catheter assembly 500 and the needle shielding device 100.

Another embodiment is shown in FIG. 11*a*, and is a connection and rotational securement involving that the blinkers 250 of the inner part 230 comprises blinker ribs 253 which each engages a connection portion recess 527 on an external side of the connection portion 525.

Yet another embodiment is shown in FIG. 11*b*. In this configuration, the inside of the blinkers 250 comprises blinker recesses 256 and the connection portion 525 comprises external connection portion ribs 528.

Preferably, the connection portion recesses 527 and the blinker recesses 256 shown in FIGS. 11*a* and 11*b* are tapered. This results in that when the blinker ribs 253 (or the connection portion ribs 528) are pressed further into the connection portion recesses 527 (or the blinker recesses 256), the engagement between the connection ribs 253 and the connection portion recesses 527 (or the engagement between the connection portion ribs 530 and the blinker recesses 256) becomes firmer.

Further, when using the inner part 130, the grip part 110 comprises internal grip part recesses 117, which engage connection portion ribs 530 and yields a very rotationably stable connection between the catheter assembly 500 and the needle shielding device 100 during the application of the needle 115 to the patient.

The rotational securement and the rectangular lateral cross section provides a stable needle shielding device 100 which is prevented from rotating during use. This allows for a controlled telescopic extraction of the grip part 110 and middle part 120, 220 along the inner part 130, 230.

Also, the grip part 110, the middle part 120, 220, and the inner part 130, 230 may be shorter or longer than each other or be of the same length (in the direction extending along the axis A).

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

The invention claimed is:

1. A needle shielding device for a catheter instrument extending along a longitudinal axis A, comprising:

- an inner part comprising an inner part track extending along said axis A;
- a middle part comprising a middle part track extending along said axis A, and an internal middle part engagement;

an outer grip part, comprising a needle hub, holding a needle extending along said axis A, and a grip part internal engagement;

wherein said grip part internal engagement is configured to slidingly engage said middle part track, and said middle part engagement is configured to slidingly engage said inner part track such that the inner part, the middle part and the outer grip part are telescopingly slidable in relation to one another;

wherein the needle shielding device, and the outer grip, middle and inner parts have a substantially rectangular lateral cross-section, and wherein the inner part track and the middle part track are located along a corner of the rectangular lateral cross-section of the inner part and the middle part, respectively; and wherein the needle shielding device further comprises a needle tip shielding device arranged on a proximal end thereof, the needle tip shielding device being connected to an inner part proximal end, and wherein the needle tip shielding device is protected by at least two edge blinkers arranged at the inner part proximal end.

2. The needle shielding device according to claim 1, wherein the middle part and the inner part each comprise a middle part abutment and an inner part abutment.

3. The needle shielding device according to claim 1, wherein the needle tip shielding device being connected to an inner part proximal side edge, and wherein the at least two edge blinkers extending proximally longitudinally from the inner part proximal side edge.

4. A needle shielding device for a catheter instrument extending along a longitudinal axis A, comprising:

an inner part comprising an inner part track extending along said axis A;

a middle part comprising a middle part track extending along said axis A, and an internal middle part engagement;

an outer grip part, comprising a needle hub, holding a needle extending along said axis A, and a grip part internal engagement;

wherein said grip part internal engagement is configured to slidingly engage said middle part track, and said middle part engagement is configured to slidingly engage said inner part track such that the inner part, the middle part and the outer grip part are telescopingly slidable in relation to one another; and wherein the needle shielding device further comprises a needle tip shielding device arranged on a proximal end thereof, preferably the needle tip shielding device being connected to an inner part proximal end, and wherein the needle tip shielding device is protected by at least two edge blinkers arranged at the inner part proximal end.

5. The needle shielding device according to claim 4, wherein the needle shielding device and the grip, middle and inner parts have a substantially rectangular lateral cross-section, and wherein the inner part track and the middle part track are located at a corner of the rectangular lateral cross-section of the inner part and the middle part, respectively.

6. The needle shielding device according to claim 4, wherein the middle part and the inner part each comprise a middle part abutment and an inner part abutment, respectively, and wherein said middle part abutment is configured to engage the grip part internal engagement when the middle part abutment comes into contact with the grip part engagement, and wherein said inner part abutment is configured to engage the middle part engagement when the inner part abutment comes into contact with the middle part engagement.

7. The needle shielding device according to claim 4, wherein the middle part further comprises middle part grip ribs.

8. The needle shielding device according to claim 4, wherein the middle part and the inner part each comprise a middle part groove and inner part groove, wherein said grooves extend along the axis A and are arranged on a bottom surface, a top surface, a corner or a side surface of the middle part and inner part, respectively.

9. A needle shielding device for a catheter instrument comprising:

an inner part comprising an inner part track extending along an axis A;

an outer grip part comprising a needle hub, holding a needle extending along said axis A, and a grip part internal engagement;

wherein said grip part internal engagement is configured to slidingly engage said inner part track, such that the inner part and the outer grip part are telescopingly slidable in relation to one another; and wherein during use, the outer grip part is slidingly movable along the inner part due to that a friction force between the grip part engagement and the inner part track is smaller than a connecting force between the inner part and a catheter assembly, and wherein the inner part further comprises inner part grip ribs on an upper external side thereof, and wherein the needle shielding device further comprises a needle tip shielding device arranged on a proximal end thereof, the needle tip shielding device being connected to an inner part proximal end, and wherein the needle tip shielding device is protected by at least two edge blinkers arranged at the inner part proximal end.

10. The needle shielding device according to claim 9, wherein the at least two blinkers form an inner part end fitting into a connection portion of a catheter assembly.

11. The needle shielding device according to claim 9, wherein the needle shielding device, and the grip part and inner part thereof, have a substantially rectangular lateral cross-section.

12. The needle shielding device according to claim 9, wherein the inner part comprises a distal inner part abutment, and wherein said inner part abutments are configured to engage the grip part engagement when the inner part abutments come into contact with the grip part engagement.

13. The needle shielding device according to claim 9, wherein the inner part comprises an inner part incision at a distal end thereof, said inner part incision has a tapered portion tapering towards the inner part proximal end.

14. The needle shielding device according to claim 9, wherein the inner part comprises an inner part groove, said groove extends along the axis A and is arranged on one of a bottom surface, a top surface or a side surface inner part.

15. The needle shielding device according to claim 9, wherein the inner part further comprises a push tab, the push tab being integrally formed with the inner part and wherein an angle between a push tab upper surface and an upper push part is between 90 and 150 degrees.

16. The needle shielding device according to claim 9, wherein the needle shielding device is configured, when in a retracted configuration, partly exposes the needle, and when in an extracted configuration, encapsulates the needle.

17. The needle shielding device according to claim 9, wherein the needle shielding device further comprises a rotation securement preventing rotation between the needle shielding device and a connection portion of a catheter assembly.

18. The needle shielding device according to claim 9, wherein the grip part further comprises grip side surface ribs.

19. The needle shielding device according to claim 9, wherein the middle part comprises a middle part incision and the inner part comprises an inner part incision, one of said middle part incision or said inner part incision has a tapered portion tapering towards the middle part proximal end or inner part proximal end, respectively.

* * * * *